(12) United States Patent
Davis et al.

(10) Patent No.: US 6,794,508 B2
(45) Date of Patent: Sep. 21, 2004

(54) PROCESS

(75) Inventors: Roman Davis, Durham, NC (US); Alan Millar, Durham, NC (US); Jeffrey Thomas Sterbenz, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/415,922

(22) PCT Filed: Nov. 2, 2001

(86) PCT No.: PCT/US01/48173

§ 371 (c)(1),
(2), (4) Date: May 5, 2003

(87) PCT Pub. No.: WO02/46207

PCT Pub. Date: Jun. 13, 2002

(65) Prior Publication Data

US 2004/0049042 A1 Mar. 11, 2004

(30) Foreign Application Priority Data

Nov. 3, 2000 (GB) ............................................. 0026876

(51) Int. Cl.[7] ...................... C07D 221/18; C07D 221/04
(52) U.S. Cl. .......................................... 546/77; 546/61
(58) Field of Search ...................... 546/77, 61; 514/284

(56) References Cited

FOREIGN PATENT DOCUMENTS

| EP | 0 155 096 | | 9/1985 | |
|---|---|---|---|---|
| GB | 2 264 494 | | 9/1993 | |
| WO | WO 95/07926 | * | 3/1995 | ................. 514/284 |

OTHER PUBLICATIONS

Pande, P.P. et al., "Catalytic Transfer Hydrogenation of Unsaturated Ketones and Imides Via Ammonium Formate," *Synthetic Communications*, vol. 28, No. 22, 1998, pp4193–4200. .

Rasmusson, G.H. et al., "Azasteroids as Inhibitors of Rat Prostatic 5Alpha–Reductase," *Journal of Medicinal Chemistry*, vol. 27, No. 12 Dec. 1, 1984, pp. 1690–1701.

Rasmusson, G.H. et al., "Azasteroids: Structure–Activity Relationships for Inhibition of 5Alpha–Reductase and of Androgen Receptor Binding," *Journal of Medicinal Chemistry*, vol. 29, No. 11, Nov. 1, 1986, pp. 2298–2315.

Bakshi, R.K. et al., "4, 7–Dimethyl–4–azacholestan–3–one (MK–386) and related 4–azasteroids as selective inhibitors of human type 1 5–alpha–reductase," *Journal of Medicinal Chemistry*, vol. 37, No. 23, 1994, pp. 3871–3874.

Kurata et al., "Synthesis and Testosterone 5Alpha–Reductase–Inhibitory Activity of 4–Aza–5 Alpha–Androstane–17–Carboxamide Compound with Aromatic Moiety in the C–17 Carbamoyl Group," *Chemical and Pharmaceutical Bulletin*, vol. 44, No. 1, 1996, pp. 115–121.

Bakshi, R.K. et al., "4–Aza–3–oxo–5 alpha.–androst–1–ene–17.beta.–N–arylcarboxamides as Dual Inhibitors of Human Type 1 and Type 2 Steroid 5.alpha.–Reductases. Dramatic Effect of N–Aryl Substituents on Type 1 and Type 2 5.alpha.–Reductase Inhibitory Potency," *Journal of Medicinal Chemistry*, vol. 38, No. 17, Aug. 18, 1995, pp. 3189–3192.

\* cited by examiner

*Primary Examiner*—Charanjit S. Aulakh
(74) *Attorney, Agent, or Firm*—Amy H. Fix

(57) ABSTRACT

An improved process for preparing steriods, such as 3-oxo-4-azasteroids, is described. Compounds of this type are known to be useful in the preparation of compounds having 5a-reductase inhibitor activity. The process comprises the hydrogenation of the corresponding steroid alkene in the presence of ammonium acetate, ammonium formate, and/or ammonium propionate and an appropriate catalyst.

19 Claims, No Drawings

PROCESS

This application is filed pursuant to 35 U.S.C. § 371 as a United States National Phase Application of International Application No. PCT/US01/48173 filed Nov. 2, 2001; which claims priority from GB 0026876.3 filed Nov. 3, 2000.

FIELD OF THE INVENTION

The present invention relates to an improvement in a process for the preparation of steroids. More particularly, the invention Is concerned with improvements in a process for preparing steroids, such as 3-oxo-4-azasteroids, by hydrogenation of the corresponding steroid alkene. Compounds of this type are known to be useful in the preparation of compounds having 5α-reductase inhibitor activity.

BACKGROUND OF THE INVENTION

Steroid 5α-reductases catalyze conversion of testosterone to DHT in an NADPH dependent fashion as shown in Scheme A.

SCHEME A

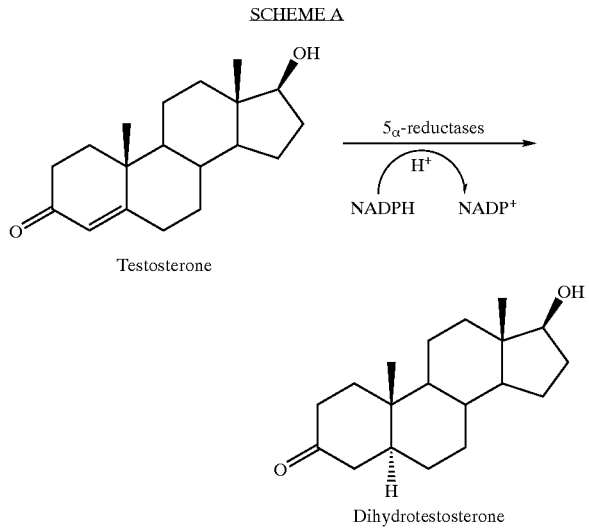

The inhibition of the conversion of testosterone to DHT is anticipated to be useful in the treatment of a variety of androgen responsive diseases, e.g., benign prostate hyperplasia, prostate cancer, acne, male pattern baldness and hirsutism. Hence, 5α-reductase inhibitors have been the subject of active research worldwide. For example, see: Hsla, S. and Voight, W., *J. Invest. Derm.*, 62, 224 (1973); Robaire, B. et al., *J. Steroid Biochem.*, 8, 307 (1977); Petrow, V. et al., *Steroids*, 38, 121 (1981); Liang, T. et al., *J. Steroid Biochem.*, 19, 385 (1983); Holt, D. et al., *J. Med. Chem.*, 33, 937 (1990); U.S. Pat. No. 4,377,584, U.S. Pat. No. 4,760,071 and U.S. Pat. No. 5,017,568. One particularly promising 5α-reductase inhibitor is MK-906 (Merck), known by the generic name, finasteride, and marketed under the trademark, Proscar, is an inhibitor of type 2 5α-reductase. In addition, dual inhibitors of type 1 and 2 human 5α-reductase are disclosed in WO 95/07926 and WO 95/07927, the contents of which are incorporated herein by reference.

Processes for the preparation of the 5α-reductase inhibitors are described in WO 95/07926, WO 95/07927, U.S. Pat. No. 4,760,071, U.S. Pat. No. 4,377,584, U.S. Pat. No. 4,179,453, U.S. Pat. No. 5,670,643 and Bhattacharya, A. et al., *J. Am. Chem. Soc.*, 110, 3318 (1988). Important intermediates in the preparation of 5α-reductase inhibitors are 4-aza-5α-androstan-3-ones, e.g. 3-oxo-4-azaandrost-17β-carboxylic acid, which can be prepared by hydrogenation of the corresponding 4-aza-androst-5-en-3-one, e.g. 3-oxo-4-azaandrost-5-en-17β-carboxylic acid. WO 95/07926 and WO95/07927 describe a process by which a 17β-substituted 4-aza-androst-5-en-3-one is converted to the corresponding 17β-substituted 4-aza-5α-androstan-3-one by hydrogenation. For example, the hydrogenation may be carried out in acetic acid at 60 to 70° C. and 276–414 kPa (40–60 psi) hydrogen pressure in the presence of catalytic platinum oxide.

The problem to be solved by the present invention is the provision of a superior, and more selective process for the hydrogenation of steroid alkenes.

SUMMARY OF THE INVENTION

Scheme 1 shows the hydrogenation of a steroid, 3-oxo-4-azaandrost-5-en-17β-carboxylic acid, to the corresponding 5α-androstane and 5β-androstane isomers. 5α-androstane isomer produced using the reaction can be used in the preparation of 5α-reductase inhibitors. For large scale manufacture, a hydrogenation process which could be carried out at atmospheric pressure was desired. However, as demonstrated by the experiments below, considerable problems relating to α:β ratios were experienced when hydrogenation was carried out at atmospheric pressure.

Scheme 1:

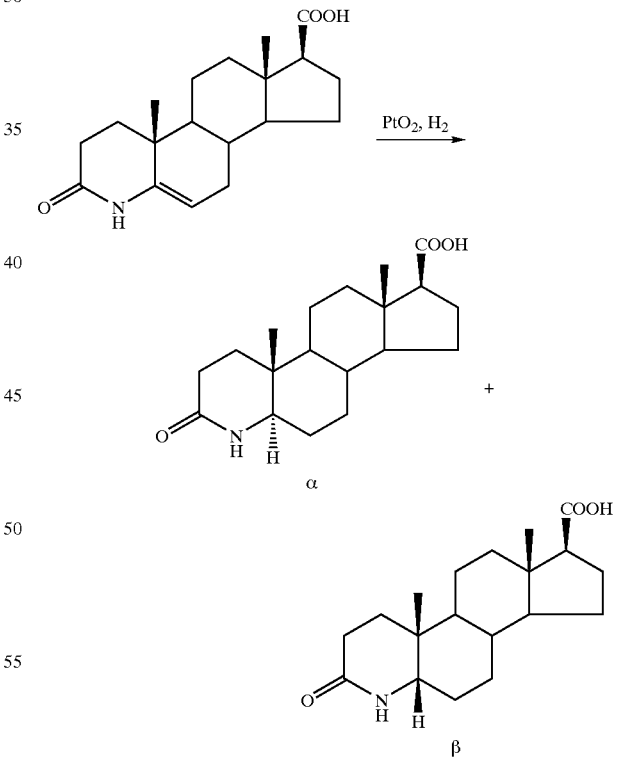

The present inventors have found a process for hydrogenating steroid alkenes which can be performed at atmospheric pressure. The problem of low α:β ratios was solved by carrying out the hydrogenation in the presence of ammonium acetate, ammonium formate or ammonium propionate.

Accordingly, the present invention provides a process for hydrogenating steroid alkenes comprising the step of hydrogenating one or more double bonds in the presence of ammonium acetate, ammonium formate, ammonium propionate, or mixtures thereof and an appropriate catalyst.

A further aspect of the invention is the use of the process of the invention in the preparation of a 5α-reductase inhibitor.

DETAILED DESCRIPTION OF THE INVENTION

The hydrogenation process provided by the present invention may be used in place of previous hydrogenation processes in the preparation of 5α-reductase inhibitors, for example, in the preparation of 5α-reductase inhibitors as described in WO 95/07926, WO95/07927, U.S. Pat. No. 4,377,584, U.S. Pat. No. 4,760,071, U.S. Pat. No. 4,179,453, U.S. Pat. No. 5,670,643, and Bhattacharya, A. et al., *J. Am. Chem. Soc.*, 110, 3318 (1988).

In one embodiment, the invention provides a process for the preparation of a steroid which comprises the hydrogenation of the corresponding steroid alkene in the presence of ammonium acetate, ammonium formate and/or ammonium propionate and an appropriate catalyst. Preferably the steroid is a 3-oxo-4-azasteroid. Preferably, the steroid alkene is a 4-aza-androsten-3-one.

In a preferred aspect of the invention, the 3-oxo-4-azasteroid is a compound of formula (I)

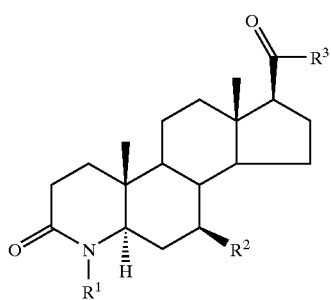

(I)

wherein:
  $R^1$ represents hydrogen, OH, $C_{1-6}$ alkyl, aryl or a heteroaromatic group;
  $R^2$ represents hydrogen, $C_{1-6}$ alkyl, aryl or a heteroaromatic group;
  $R^3$ represents hydrogen, OH, $C_{1-6}$ straight or branched chain alkyl, $C_{1-6}$ straight or branched chain alkoxy, aryl, heteroatom, or NHQ wherein Q represents hydrogen, OH, $C_{1-6}$ straight or branched chain alkyl, $C_{1-6}$ straight or branched chain alkoxy, (A)

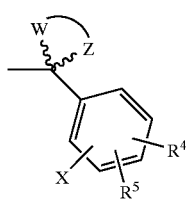

(A)

wherein $R^4$ and $R^5$ are independently hydrogen, lower alkyl, lower alkoxy, trifluoromethyl, cyano, halogen, phenyl (optionally substituted with one or more halogens), or when $R^4$ and $R^5$ are on adjacent carbons, taken together form a fused 5, 6 or 7 member ring optionally containing one or more oxygen or sulfur atoms;

W and Z are methylene groups which taken together with the carbon to which they are attached form a saturated, 3 to 12 member ring system optionally:
  1) substituted independently with one or more lower alkyl groups,
  2) containing an oxygen or sulfur atom,
  3) two said methylene groups of said 3 to 12 member ring are joined with a ($C_{1-6}$) alkylene group to form a bicyclic ring system; and
X is hydrogen or halogen; or (B)

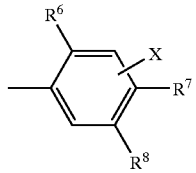

(B)

wherein $R^6$ is trifluoromethyl, phenyl optionally substituted with one or more halogens or branched ($C_{4-7}$) alkyl groups, or branched ($C_{4-7}$) alkyl;
  either of $R^7$ or $R^8$ is trifluoromethyl, halogen, phenyl optionally substituted with one or more halogens or branched ($C_{4-7}$)alkyl groups, or branched ($C_{4-7}$) alkyl, while the other is hydrogen or halogen; and
  X is hydrogen or halogen.

Preferably the 4-aza-androsten-3-one is 4-aza-androst-5-en-3-one. More preferably the 4-aza-androst-5-en-3-one is a compound of formula (II):

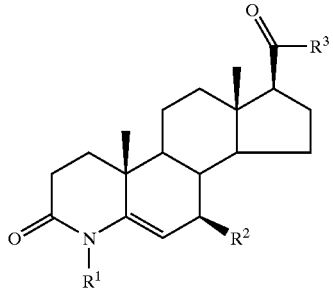

(II)

wherein the R groups are as defined above.

As used herein the term "lower" in relation to alkyl and alkoxy means 1 to 6 carbons, especially 1 to 4, straight or branched. As used herein the term "branched ($C_{4-7}$) alkyl" means 3–6 carbons attached via a quaternary carbon, e.g., t-butyl, t-amyl, etc.

As used herein, the term "heteroaromatic group" means rings containing one or more heteroatoms selected from nitrogen, sulphur and oxygen atoms. Examples of 5-membered groups include thiophene, thiazole, pyrrole, pyrazole, imidazole and furan, whilst 6-membered groups include pyridyl, pyrazyl and pyrimidyl.

As used herein, the term "halogen" means fluorine, chlorine, bromine and iodine.

As used herein, the term "steroid" means a tetracyclic cyclopenta[a]phenanthrene.

As used herein, the term "steroid alkene" means a steroid having one or more double bonds.

Preferably, $R^1$ is hydrogen.
Preferably $R^2$ is hydrogen.
Preferably $R^3$ is hydrogen, OH, $C_{1-4}$ alkyl, $C_{1-4}$ alkoxy or NHQ. More preferably $R^3$ is hydrogen.

Preferably Q is hydrogen, OH, $C_{1-6}$ straight or branched chain alkyl, $C_{1-6}$ straight or branched chain alkoxy, or (B)

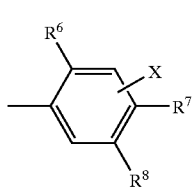

(B)

wherein $R^6$ is trifluoromethyl or branched ($C_{4-7}$) alkyl; either of $R^7$ or $R^8$ is trifluoromethyl while the other is hydrogen; and X is hydrogen. More preferably Q is hydrogen, $C_{1-4}$ straight or branched chain alkyl or 2,5-bis (trifluoromethyl))phenyl. Most preferably Q is tert-butyl or 2,5-bis(trifluoromethyl))phenyl.

It is to be understood that the present invention covers all combinations of suitable, convenient and preferred groups described hereinabove.

The hydrogenation process is suitably carried out in the presence of ammonium acetate, ammonium formate and/or or ammonium propionate. Ammonium acetate, ammonium formate, ammonium propionate or a mixture thereof are suitably present in the range 1–25% w/w compared to substrate, preferably 2–10%, more preferably 2.5–5%, most preferably approximately 2.5%. The hydrogenation process is preferably carried out in the presence of ammonium acetate. Preferably the ammonium acetate, ammonium formate and/or ammonium propionate is added to the reaction mixture at the start of the reaction.

Suitable catalysts for the hydrogenation reaction are: $Pt_2O$, Pt/C, Pd/C, $Pd(OH)_2$ and Ni catalysts. Preferably the catalyst is $Pt_2O$, Pt/C, Pd/C or $Pd(OH)_2$, more preferably $Pt_2O$.

The process of the invention is suitably carried out at a pressure range 103–3447 kPa (15–500 psi). Preferably the pressure range is 103–414 kPa (15–60 psi).

The process of the invention is suitably carried out at temperature 50–75° C. Preferably at approximately 55° C.

4-aza-androsten-3-ones may be prepared by any method known in the art for the preparation of compounds of analogous structure. For example, a suitable method for the preparation of compounds of formula (II) is disclosed in WO 95/07926.

Those skilled in the art will appreciate that in the preparation of the compound of formula (I) or a solvate thereof it may be necessary and/or desirable to protect one or more sensitive groups in the molecule to prevent undesirable side reactions. The protecting groups used in the preparation of the compound of formula (I) may be used in a conventional manner. See for example Protective Groups in Organic Chemistry, Ed. J. F. W. McOmie, Plenum Press, London (1973) or Protective Groups in Organic Synthesis, Theodora Green, John Wiley and Sons, New York (1981).

The process of the invention can be used in the preparation of 5α-reductase inhibitors by any method known in the art, for example as described in WO 95/07926, WO95/07927, U.S. Pat. No. 4,377,584, U.S. Pat. No. 4,760,071, U.S. Pat. No. 4,179,453, U.S. Pat. No. 5,670,643, Bhattacharya, A. et al., *J. Am. Chem. Soc.*, 110, 3318 (1988), and as shown in the Examples. A further aspect of the invention is therefore the use of the process of the invention in the preparation of a 5α-reductase inhibitor, such as, 17β-(N-t-butylcarbamoyl)-4-aza-5α-androst-1-en-3-one or 17β-N-(2,5-bis(trifluoromethyl))phenylcarbamoyl-4-aza-5α-androst-1-en-3-one. In other words, a 5α-reductase inhibitor, such as 17β-(N-t-butylcarbamoyl)4-aza-5α-androst-1-en-3-one or 17β-N-(2,5-bis(trifluoromethyl)) phenylcarbamoyl-4-aza-5α-androst-1-en-3-one, may be prepared using a process comprising the process of the invention. In the preparation of 5α-reductase inhibitors it will be understood that the process of the invention may be used either for the elimination of a double bond at an intermediate stage in the preparation of the 5α-reductase inhibitor, or as the last main step in a preparative sequence. For example, in the preparation of 17β-N-(2,5-bis (trifluoromethyl))phenylcarbamoyl-4-aza-5α-androst-1-en-3-one the hydrogenation process may be used for the elimination of a double bond at an intermediate stage in preparation, see for example Scheme 2 below. Preferably, 17β-N-(2,5-bis(trifluoromethyl))phenylcarbamoyl-4-aza-5α-androst-1-en-3-one is prepared by a method comprising the process of the invention, e.g. hydrogenating a compound of formula (II) to a compound of formula (I), followed by:

(i) dehydrogenation, e.g. of a compound of formula (I) such as 4-aza-5α-androstan-3-one-17β-carboxylic acid, to insert a double bond between carbons 1 and 2;

(ii) reaction with the compound of formula (III)

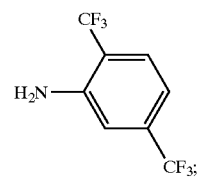

(III)

and (iii) if necessary and/or desired, subjecting the compound thus obtained to one or more further reactions comprising;

(a) removing any protecting group or groups; and/or
(b) converting the compound or a solvate thereof into a pharmaceutically acceptable solvate thereof.

The following examples illustrate aspects of this invention but should not be construed as limiting the scope of the invention in any way.

EXAMPLES

Example 1

Preparation of 17β-N-(2,5-bis(trifluoromethyl)) phenylcarbamoyl-4-aza-5α-androst-1-en-3-one Scheme 2:

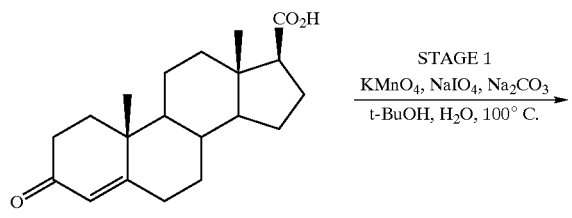

STAGE 1
$KMnO_4$, $NaIO_4$, $Na_2CO_3$
t-BuOH, $H_2O$, 100° C.

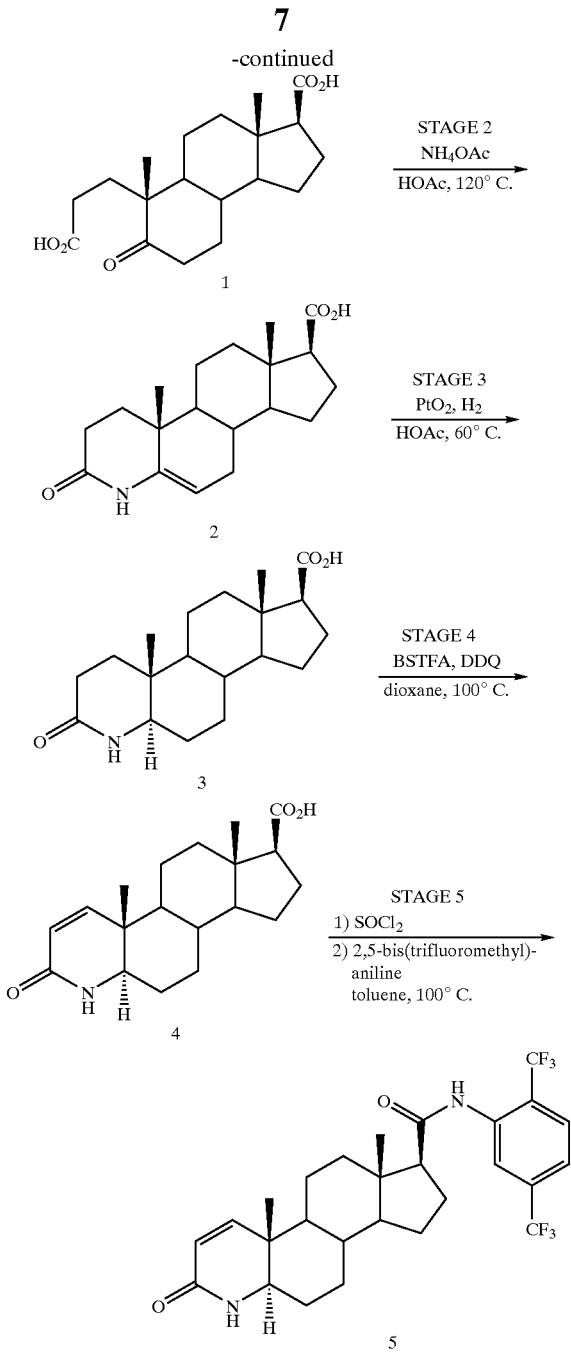

Stage 1: 17β-carboxy-5-oxo-A-nor-3,5-secoandrostan-3-oic Acid (1)

Typical scale 34.0 kg

A solution of sodium periodate (183 kg, 7.9 eq.) and potassium permanganate (1.4 kg, catalytic.) in water (410 l) was heated at 75–80° C. with stirring to effect solution. A mixture of 3-oxo-4-androstene-17βcarboxylic acid (CC14837, 17-ADCA) (34.0 kg, 1 eq.), $Na_2CO_3$ (29 kg, 2.5 eq.), tert-butanol (580 l) and water (60 l) was heated at reflux (75–80° C.) under a nitrogen atmosphere. The aqueous solution of sodium periodate/potassium permanganate was added to the refluxing CC14837/t-butanol/water slurry, allowing for evolution of carbon dioxide at a controlled rate. Water (25 l) was used as a line wash following the addition. The mixture was heated at reflux (75–80° C.) for about 1 hour. The mixture was cooled, and acetic acid (135 l) added while the contents were further cooled. The mixture was filtered, and the filter cake washed with tert-butanol (130 l) and acetic acid (135 l). The filtrate/wash was transferred back into the reaction vessel through a filter, and vacuum distilled at <65° C. Water (1000 l) was added while the slurry was stirred. The product was collected by filtration, washed with water and dried in vacuo at up to 80° C. with a nitrogen purge. Weight range: 20–23 kg (58–66% theory, 59–67% w/w).

Stage 2: 3-oxo-4-aza-5-androstene-17β-carboxylic Acid (2).

Typical scale 54.0 kg

A mixture of the Seco-Acid 1 (54.0 kg, 1 eq.), $NH_4Oac$ (47 kg, 4.1 equiv.) and HOAc (190 l) were stirred at reflux for at least three hours. The mixture was cooled and water (190 l) was added. The mixture was stirred for at least 2 hours. The product was isolated by filtration, washed with water and dried at up to 55° C. under vacuum with a nitrogen purge. Weight range: 45–51 kg (85–95% theory, 83–93% w/w).

Stage 3: 4-aza-5α-androstan-3-one-17β-carboxylic Acid (3).

Typical scale 33.5 kg

The hydrogenation vessel was charged with acetic acid (530 l), 3-oxo-4-aza-5-androstene-17β-carboxylic acid 2 (33.5 kg.), and ammonium acetate (1.0 kg, 0.1 eq.). After purging at 20–25° C. with nitrogen, the platinum oxide catalyst (3.0 kg.) was charged, the stirrer started and the temperature adjusted to 20–25° C. After purging with hydrogen, the stirring batch was allowed to take up hydrogen. After 30 minutes at ≦30° C., the temperature was adjusted to 60–65° C., and stirring continued until hydrogen uptake ceased. After purging with nitrogen, Solka Floc (1.7 kg.) was charged, and the hot reaction mixture recirculated through a filter until the solution was clear. The hot reaction filtrate was transferred to a clean vessel. The reactor was rinsed with hot acetic acid (100 l.), and the rinse was recirculated as a wash through the filter. The combined filtrates/wash were distilled under vacuum at ≦70° C. to about 3.6 volumes. The resulting slurry was cooled to ≦25° C. Methanol (130 l.) was added and the mixture stirred for at least 2 hours at ≦25° C. The product was collected by filtration; the cake washed with methanol and dried in vacuo at ≦60° C. Weight range: 25–28.5 kg (75–85% theory, 75–85% w/w).

Stage 4: 4-aza-5α-androst-1-ene-3-one-17β-carboxylic (4).

Typical scale 20.0 kg

The reaction vessel was charged with dioxane (180 l), 4-aza-5α-androstan-3-one-17β-carboxylic acid 3 (20.0 kg, 1 eq.) and 2,3-dichloro-5,6-dicyanobenzoquinone (DDQ) (15.6 kg, 1.1 eq.). Bis(trimethylsilyl)trifluoroacetamide (BSTFA) (78 l, 4.7 eq.) was added. The reaction mixture was heated to reflux and maintained at reflux for 2–4 hours. The mixture was cooled to ≦30° C. and transferred to a second vessel containing a stirring mixture of dichloromethane (440 l) and a 1% aqueous solution of sodium metabisulfite (150 l). Dioxane (80 l) was used as a vessel and line wash to ensure complete transfer. The resultant mixture was stirred at <25° C. for 45–90 minutes. The mixture was filtered, the filter cake washed with dichloromethane (105 l), and the combined filtrates allowed to settle before phase separation. The organic layer was washed with 1N hydrochloric acid (125 l), diluted with acetonitrile (220 l) and concentrated in vacuo to eight volumes. Acetonitrile (220 l) was added and the resultant slurry cooled to ≦5° C. The crude product was collected by filtration and washed with acetonitrile (40 l). The crude product was reslurried in refluxing acetonitrile (200 l) for at least 1 hour, cooled and aged for at least 1 hour at ≦5° C. The solid was collected by filtration, washed with acetonitrile (30 l.) and dried in vacuo at ≦60° C. Weight range: 14–18 kg (70–85% theory, 70–85% w/w).

Stage 5: (5α,17β)-N-[2,5-bis(trifluoromethyl)phenyl]-3-oxo-4-azaandrost-1-ene-17-carboxamide (5).

Typical scale 18.0 kg

A mixture of 4-aza-5α-androst-1-ene-3-one-17β-carboxylic acid 4 (18.0 kg, 1 eq.), toluene (540 l), pyridine (11.2 kg, 2.5 eq.) and dimethylformamide (0.2 kg, cat.) was stirred and cooled to ≦−5° C. Thionyl chloride (8.1 kg, 1.2 eq.) in toluene (9 l) was added, at such a rate that the temperature was maintained at ≦0° C. The mixture was maintained for 2–3 hours at 15–25° C. To the mixture 2,5-bis(trifluoromethyl)aniline (14.2 kg, 1.1 eq.) and dimethylaminopyridine (0.14 kg, cat.) were added using toluene (9 l) as a line wash to ensure complete transfer. The mixture was heated at 95–105° C. for 18–24 hours. The reaction completion may be monitored by in-process check (HPLC). After cooling, the solids were removed by filtration and washed with ethyl acetate (270 l). The combined filtrate/wash was extracted four times with 10% potassium hydroxide (57 l each). The organic solution was washed with 1N hydrochloric acid (57 l) and water (57 l). The resulting solution was concentrated in vacuo at ≦80° C. to four volumes. Pyridine (290 l) was added, and the solution is again concentrated in vacuo to four volumes. Pyridine (72 l) was added, and the solution is again concentrated in vacuo to 4 volumes. The solution was clarified, the vessel and line were washed through with pyridine (18 l) to ensure complete transfer, and filtered acetonitrile (18 l) was added. The stirring solution was warmed to 45–55° and water (110 l) was added slowly in portions to effect crystallization. The resulting slurry was cooled to <15° C., stirred for 1–2 hours, and the solid collected by filtration in a filter-dryer. The reactor was rinsed with 1:1 pyridine:water (36 l), and the rinse directed as a wash to the filter cake. The reactor was further rinsed with filtered acetonitrile (45 l), and the rinse directed to the filter cake. The intermediate-grade product and filtered acetonitrile (54 l) was stirred and heated in the filter-dryer to reflux, then cooled to ≦15° C. and filtered. The solid was washed with acetonitrile (18 l). The resulting solid and filtered acetonitrile (110 l) were stirred and heated in the filter-dryer at reflux for 2–3 hours. The mixture was then chilled to ≦15° C. and filtered. The solid was washed with acetonitrile (18 l). The solid was dried in vacuo at ≦90° C. Offloading via the filter-dryer chute gave the product as a white to off-white solid. Weight range: 11 to 17 kg (37–57% theory, 61–94% w/w).

Example 2

Influence of Ammonium Acetate on the Hydrogenation of 3-oxo-4azaandrost-5-ene-17β-carboxylic Acid Scheme 3:

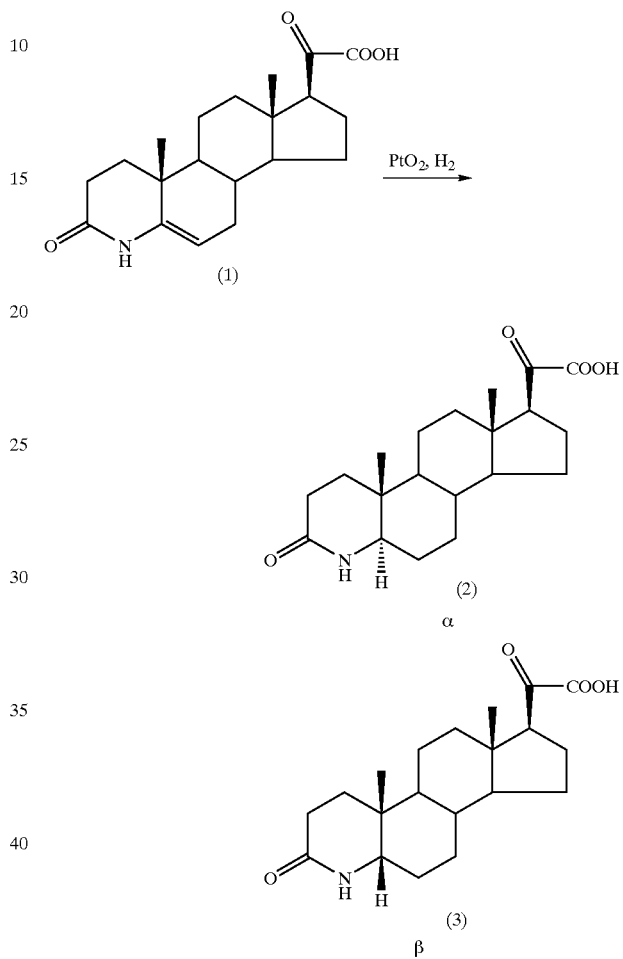

Experimental

The hydrogenation vessel was charged with HOAc (16 vol.), 3-oxo-4-azaandrost-5-ene-17β-carboxylic acid (1 wt), and NH$_4$OAc (0.025 wt), while maintaining the temperature at 20–25° C. The system was purged three times with N$_2$. The PtO$_2$ (0.12 wt) was charged, stirring was initiated and the temperature was adjusted to 20–25° C. The vessel was again purged three times with N$_2$; following the third purge, stirring was stopped and the vessel purged three times with H$_2$. Stirring was resumed and the batch allowed to take up hydrogen. The temperature was maintained at 20–25° C. for the first 30 minutes, adjusted to 60–65° C. over 30 minutes, and maintained until the reaction was complete. Following reaction completion, stirring was stopped and the vessel was purged three times with N$_2$. Solka Floc (0.05 wt) was charged and stirring was resumed. The hot reaction mixture was recirculated through a GAF filter until the solution was clear and the hot reaction filtrate was then transferred to a clean vessel. The reaction vessel was charged with HOAc (3 vol.), heated to 60–65° C. and stirred for at least 5 minutes. The hot rinse was filtered through the GAF filter and combined with the reaction filtrate. Volume was reduced in vacuo to 3.6 volumes and the resulting slurry was cooled to 20–25° C. Methanol (4 vol) was added to the slurry and the mixture was "aged" to obtain a more filterable particle for 2–24 hours at 20–25° C. The product was isolated by filtration and washed with methanol (1.5 vol). The resulting solid was dried on the filter for at least 30 minutes, then dried in vacuo at 50–60° C. for 12–18 hours.

Results

Following successful campaigns using 276–345 kPa (40–50 psi) $H_2$ pressure, where $\alpha:\beta$ ratios had been >9:1, manufacturing constraints necessitated additional investigations at atmospheric $H_2$ pressure. Unfortunately, atmospheric hydrogenation resulted in $\alpha:\beta$ ratios of <5:1. In a comparable study conducted on a 17β-alkyl 4-azaandrost-5-ene, Miller et al. (Tetrahedron Letters 36(44): 7949–7952, 1995) screened a variety of catalysts in high pressure hydrogenation. Other catalysts were screened, but $\alpha:\beta$ ratios of acceptable levels could not be achieved at atmospheric hydrogenation. However, it was surprisingly found that addition of 2.5–10% (w/w vs. substance) of $NH_4OAc$ restored $\alpha:\beta$ ratios to >10:1 (Table 1). Contrary to literature precedent, ammonium chloride was not effective. Also ineffective were ammonium dihydrogen phosphate, and sodium acetate. Tetramethylethylenediammonium (TMEDA) acetate, was effective at improving the $\alpha:\beta$ ratio, but significantly retarded the hydrogenation.

The results of a pilot study at 0%, 2.5% and 10% $NH_4OAc$ loads are shown in Table 2. Atmospheric hydrogenation at 2.5 w/w % $NH_4OAc$ load was successfully applied to batches of >30 kg input each (Table 3), supplying 83–85% isolated yields of 3-oxo-4-aza-5α-androstane (2) of >99% purity.

TABLE 1

Various Additives/Modifiers

| | INPUT (g) | | OUTPUT | | | |
|---|---|---|---|---|---|---|
| 1 | $PtO_2$ | additive (2.5% w/w) | 1(%) | 2(%) | 3(%) | $\alpha:\beta$ ratio |
| 20 | 2.4 | None | nd | 85.96 | 12.94 | 4.6 |
| 20 | 2.4 | $NH_4OAc$ | nd | 91.83 | 6.83 | 13.4 |
| 20 | 2.4 | $NH_4H_2PO_4$ | 84.51 | 3.19 | 7.21 | 0.4 |
| 20 | 2.4 | TMEDA | 87.24 | 10.95 | 0.6 | 18.2 |
| 20 | 2.4 | NaOAc | nd | 84.00 | 141.13 | 6.0 | nd = not detected

TABLE 2

$\alpha:\beta$ Ratio at Various $NH_4OAc$ Loads/1 atm. $H_2$

| $NH_4OAc$ | In-Process HPLC Data (area %) | | | | Th. Yield |
|---|---|---|---|---|---|
| (%) | % (1) | % α (2) | % β (3) | $\alpha:\beta$ ratio | % |
| 0.0 | Nd | 78.8 | 20.8 | 3.8 | 79 |
| 2.5 | Nd | 90.5 | 7.5 | 12.1 | 92 |
| 10.0 | 3.5 | 89.0 | 6.9 | 12.9 | 93 |

TABLE 3

$\alpha:\beta$ Ratio and Yield (at 2.5% $NH_4OAc$ load/1 atm $H_2$)

| INPUT (kg) | | | In-Process HPLC Data (area %) | | | OUTPUT yield (2) | | |
|---|---|---|---|---|---|---|---|---|
| (1) | $PtO_2$ | $NH_4OAc$ | % (1) | % α (2) | % β (3) | $\alpha:\beta$ ratio | kg | % |
| 0.2 | 0.02 | 0.005 | nd | 90.5 | 7.5 | 12.1 | 0.17 | 83.0 |
| 33.5 | 4 | 0.84 | 0.5 | 91.3 | 8.2 | 11.1 | 28.5 | 84.7 |
| 33.5 | 4 | 0.84 | 0.3 | 92.9 | 6.8 | 13.7 | 28.3 | 84.0 |

What is claimed is:

1. A process for the preparation of a 3-oxo-4-azasteroid from a corresponding 4-aza-androsten-3-one steroid alkene comprising the step of hydrogenating one or more double bonds in the presence of ammonium acetate, ammonium formate, ammonium propionate, or mixtures thereof and an appropriate catalyst.

2. A process as claimed in claim 1 wherein the 4-aza-androsten-3-one is a 4-aza-androst-5-en-3-one.

3. A process as claimed in claim 1 wherein the 3-oxo-4-azasteroid is a compound of formula (I):

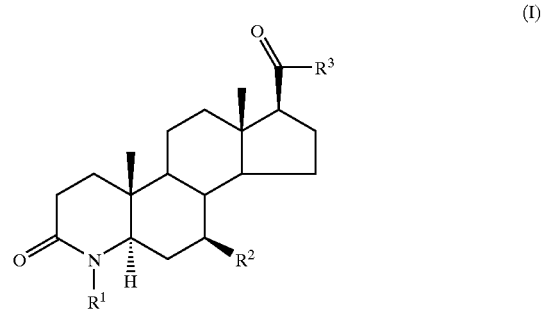

(I)

wherein:
$R^1$ represents hydrogen, OH, $C_{1-6}$ alkyl, aryl or a heteroaromatic group;
$R^2$ represents hydrogen, $C_{1-6}$ alkyl, aryl or a heteroaromatic group;
$R^3$ represents hydrogen, OH, $C_{1-6}$ straight or branched chain alkyl, $C_{1-6}$ straight or branched chain alkoxy, aryl, heteroaromatic group, or NHQ wherein Q represents hydrogen, OH, $C_{1-6}$ straight or branched chain alkyl, $C_{1-6}$ straight or branched chain alkoxy, (A)

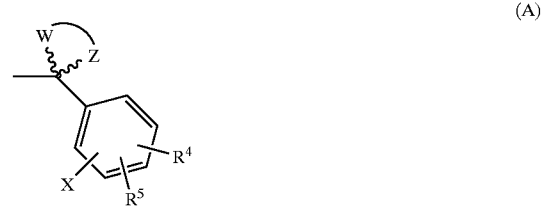

(A)

wherein $R^4$ and $R^5$ are independently hydrogen, lower alkyl, lower alkoxy, trifluoromethyl, cyano, halogen, phenyl (optionally substituted with one or more halogens), or when $R^4$ and $R^5$ are on adjacent carbons, taken together form a fused 5, 6 or 7 member ring optionally containing one or more oxygen or sulfur atoms;
W and Z are methylene groups which taken together with the carbon to which they are attached form a saturated, 3 to 12 member ring system optionally:

1) substituted independently with one or more lower alkyl groups,
2) containing an oxygen or sulfur atom,
3) two said methylene groups of said 3 to 12 member ring are joined with a ($C_{1-6}$) alkylene group to form a bicyclic ring system; and X is hydrogen or halogen
or (B)

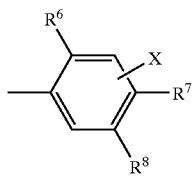

(B)

wherein $R^6$ is trifluoromethyl, phenyl optionally substituted with one or more halogens or branched ($C_{4-7}$) alkyl groups, or branched ($C_{4-7}$) alkyl;
either of $R^7$ or $R^8$ is trifluoromethyl, halogen, phenyl optionally substituted with one or more halogens or branched ($C_{4-7}$)alkyl groups, or branched ($C_{4-7}$) alkyl, while the other is hydrogen or halogen; and
X is hydrogen or halogen.

4. A process as claimed in claim 2 wherein the 4-aza-androst-5-en-3-one is a compound of formula (II)

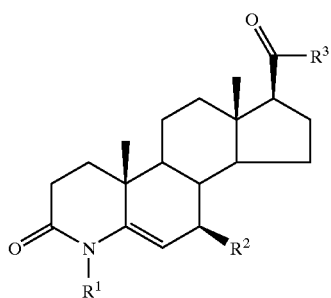

(II)

wherein:
$R^1$ represents hydrogen, OH, $C_{1-6}$ alkyl, aryl or a heteroaromatic group;
$R^2$ represents hydrogen, $C_{1-6}$ alkyl, aryl or a heteroaromatic group;
$R^3$ represents hydrogen, OH, $C_{1-6}$ straight or branched chain alkyl, $C_{1-6}$ straight or branched chain alkoxy, aryl, heteroaromatic group, or NHQ wherein Q represents hydrogen, OH, $C_{1-6}$ straight or branched chain alkyl, $C_{1-6}$ straight or branched chain alkoxy, (A)

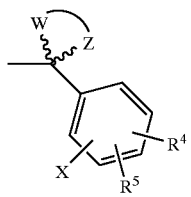

(A)

wherein $R^4$ and $R^5$ are independently hydrogen, lower alkyl, lower alkoxy, trifluoromethyl, cyano, halogen, phenyl (optionally substituted with one or more halogens), or when $R^4$ and $R^5$ are on adjacent carbons, taken together form a fused 5, 6 or 7 member ring optionally containing one or more oxygen or sulfur atoms;
W and Z are methylene groups which taken together with the carbon to which they are attached form a saturated, 3 to 12 member ring system optionally:
1) substituted independently with one or more lower alkyl groups,
2) containing an oxygen or sulfur atom,
3) two said methylene groups of said 3 to 12 member ring are joined with a ($C_{1-6}$) alkylene group to form a bicyclic ring system; and X is hydrogen or halogen
or (B)

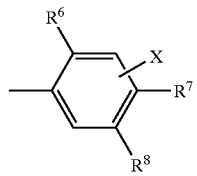

(B)

wherein $R^6$ is trifluoromethyl, phenyl optionally substituted with one or more halogens or branched ($C_{4-7}$) alkyl groups, or branched ($C_{4-7}$) alkyl;
either of $R^7$ or $R^8$ is trifluoromethyl, halogen, phenyl optionally substituted with one or more halogens or branched ($C_{4-7}$)alkyl groups, or branched ($C_{4-7}$) alkyl, while the other is hydrogen or halogen; and
X is hydrogen or halogen.

5. A process as claimed in claim 3 wherein $R^1$ is hydrogen; $R^2$ is hydrogen; $R^3$ is hydrogen, OH, $C_{1-4}$ alkyl, $C_{1-4}$ alkoxy or NHQ.

6. A process as claimed in claim 5 wherein Q is hydrogen, OH, $C_{1-6}$ straight or branched chain alkyl, $C_{1-6}$ straight or branched chain alkoxy, or (B)

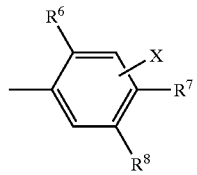

(B)

wherein $R^6$ is trifluoromethyl or branched ($C_{4-7}$) alkyl; either of $R^7$ or $R^8$ is trifluoromethyl while the other is hydrogen; and X is hydrogen.

7. A process as claimed in claim 6 wherein Q is hydrogen, $C_{1-4}$ straight or branched chain alkyl or 2,5-bis(trifluoromethyl)phenyl.

8. The process as claimed in claim 1 wherein the process is carried out in the presence of ammonium acetate.

9. The process as claimed in claim 8 wherein the ammonium acetate is present in the range 1–25% w/w.

10. The process as claimed in claim 9 wherein the ammonium acetate is present in the range 2.0–10% w/w.

11. The process as claimed in claim 1 wherein the catalyst is selected from $Pt_2O$, Pt/C, Pd/C, $Pd(OH)_2$, and Ni catalysts.

12. The process as claimed in claim 11 wherein the catalyst is selected from $Pt_2O$, Pt/C, Pd/C or $Pd(OH)_2$.

13. The process as claimed in claim 12 wherein the catalyst is $Pt_2O$.

14. The process as claimed in claims 1 wherein the process is carried out within the pressure range 103–3447 kPa.

15. The process as claimed in claim 14 wherein the pressure range is 103–414 kPa.

16. The process as claimed in claim 15 wherein the process is carried out within the temperature range 50–70° C.

17. The process as claimed in claim 4 wherein $R^1$ is hydrogen; $R^2$ is hydrogen; $R^3$ is hydrogen, OH, $C_{1-4}$ alkyl, $C_{1-4}$ alkoxy, or NHQ.

18. A process as claimed in claim 17 wherein Q is hydrogen, OH, $C_{1-6}$ straight or branched chain alkyl, $C_{1-6}$ straight or branched chain alkoxy, or (B)

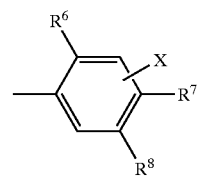
(B)

wherein $R^6$ is trifluoromethyl or branched ($C_{4-7}$) alkyl; either of $R^7$ or $R^8$ is trifluoromethyl while the other is hydrogen; and X is hydrogen.

19. A process as claimed in claim 18 wherein Q is hydrogen, $C_{1-4}$ straight or branched chain alkyl or 2,5-bis(trifluoromethyl)phenyl.

* * * * *

UNITED STATES PATENT AND TRADEMARK OFFICE
CERTIFICATE OF CORRECTION

PATENT NO. : 6,794,508 B2
APPLICATION NO. : 10/415922
DATED : September 21, 2004
INVENTOR(S) : Davis et al.

It is certified that error appears in the above-identified patent and that said Letters Patent is hereby corrected as shown below:

Title Page (56) Other Publications should read:
-- Pande, P.P. et al., "Catalytic Transfer Hydrogenation of Unsaturated Ketones and Imides Via Ammonium Formate," *Synthetic Communications*, vol. 28, No. 22, 1998, pp. 4193-4200. --

Column 1, line 10 should read:
-- invention is concerned with improvements in a process for --

Column 7, line 53 should read:
-- Stage 1: 17β-carboxy-5-oxo-A-nor-3,5-secoandrostan-3-oic Acid (1) --

Column 8, line 12 should read:
-- Stage 2: 3-oxo-4-aza-5-androstene-17β-carboxylic Acid (2). --

Column 8, line 17 should read:
-- A mixture of the Seco-Acid 1 (54.0 kg, 1 eq.), $NH_4Oac$ --

Column 8, line 25 should read:

-- Stage 3: 4-aza-5α-androstan-3-one-17β-carboxylic Acid (3). --

Column 8, line 30 should read:

-- (530 I), 3-oxo-4-aza-5-androstene-17β-carboxylic acid 2 --

Column 8, line 37 should read:

-- gen. After 30 minutes at ≤30° C. The temperature was --

Column 8, line 45 should read:

-- filtrates/wash were distilled under vacuum at ≤70° C. to --

Column 8, line 46 should read:

-- about 3.6 volumes. The resulting slurry was cooled to ≤25° --

Column 8, line 48 should read:

-- at least 2 hours at ≤25° C. The product was collected by --

UNITED STATES PATENT AND TRADEMARK OFFICE
CERTIFICATE OF CORRECTION

PATENT NO. : 6,794,508 B2
APPLICATION NO. : 10/415922
DATED : September 21, 2004
INVENTOR(S) : Davis et al.

It is certified that error appears in the above-identified patent and that said Letters Patent is hereby corrected as shown below:

Column 8, line 50 should read:

-- at ≤60° C. Weight range: 25-28.5 kg (75-85% theory, --

Column 8, line 52 should read:

-- Stage 4: 4-aza-5α-androst-1-ene-3-one-17β-carboxylic (4). --

Column 8, line 58 should read:

-- 4-aza-5α-androstan-3-one-17β-carboxylic acid 3 (20.0 kg, 1 --

Column 8, line 63 should read:

-- mixture was cooled to ≤30° C. and transferred to a second --

Column 9, line 10 should read:
-- the resultant slurry cooled to ≤5° C. The crude product was --

Column 9, line 14 should read:
-- at ≤5° C. The solid was collected by filtration, washed with --

Column 9, line 15 should read:

-- acetonitrile (30 I) and dried in vacuo at ≤60° C. Weight --

Column 9, line 18 should read:

-- Stage 5: (5α,17β)-N-[2,5-bis(trifluoromethyl)phenyl]-3-oxo-4-azaandrost-1-ene-17- carboxamide (5). --

Column 9, line 24 should read:
-- carboxylic acid 4 (18.0 kg, 1 eq.), toluene (540 I), pyridine --

Column 9, line 26 should read:
-- stirred and cooled to ≤-5° C. Thionyl chloride (8.1 kg, 1.2 --

Column 9, line 28 should read:
-- temperature was maintained at ≤0° C. The mixture was --

UNITED STATES PATENT AND TRADEMARK OFFICE
CERTIFICATE OF CORRECTION

PATENT NO. : 6,794,508 B2
APPLICATION NO. : 10/415922
DATED : September 21, 2004
INVENTOR(S) : Davis et al.

It is certified that error appears in the above-identified patent and that said Letters Patent is hereby corrected as shown below:

Column 9, line 41 should read:
-- solution was concentrated in vacuo at ≤80° C. to four --

Column 9, line 58 should read:
-- filter-dryer to reflux, then cooled to ≤15° C. and filtered. --

Column 9, line 62 should read:
-- then chilled to ≤15° C. and filtered. The solid was washed --

Column 9, line 63 should read:
-- with acetonitrile (18 I). The solid was dried in vacua at ≤90° --

Signed and Sealed this

Thirteenth Day of November, 2007

JON W. DUDAS
*Director of the United States Patent and Trademark Office*

UNITED STATES PATENT AND TRADEMARK OFFICE
CERTIFICATE OF CORRECTION

PATENT NO. : 6,794,508 B2
APPLICATION NO. : 10/415922
DATED : September 21, 2004
INVENTOR(S) : Davis et al.

It is certified that error appears in the above-identified patent and that said Letters Patent is hereby corrected as shown below:

Column 8, line 37 should read:

-- gen. After 30 minutes at ≤30° C., the temperature was --

Column 9, line 15 should read:

-- acetonitrile (30 l) and dried in vacuo at ≤60° C. Weight --

Signed and Sealed this

Twenty-ninth Day of April, 2008

JON W. DUDAS
*Director of the United States Patent and Trademark Office*